(12) United States Patent
Singla et al.

(10) Patent No.: US 9,849,090 B2
(45) Date of Patent: Dec. 26, 2017

(54) PHARMACEUTICAL COMPOSITIONS OF RIFAXIMIN

(71) Applicant: RANBAXY LABORATORIES LIMITED, New Delhi, Delhi (IN)

(72) Inventors: Ajay Kumar Singla, Gurgaon (IN); Mukesh Kumar Garg, Gurgaon (IN); Sumit Saha, Purnea (IN); Swati Aggrawal, New Delhi (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 53 days.

(21) Appl. No.: 14/650,646

(22) PCT Filed: Dec. 11, 2013

(86) PCT No.: PCT/IB2013/060829
§ 371 (c)(1),
(2) Date: Jun. 9, 2015

(87) PCT Pub. No.: WO2014/091432
PCT Pub. Date: Jun. 19, 2014

(65) Prior Publication Data
US 2015/0313848 A1    Nov. 5, 2015

(30) Foreign Application Priority Data

Dec. 12, 2012 (IN) .......................... 3823/DEL/2012

(51) Int. Cl.
| | | |
|---|---|---|
| A61K 31/437 | (2006.01) | |
| A61K 31/439 | (2006.01) | |
| A61K 9/20 | (2006.01) | |
| A61K 9/50 | (2006.01) | |
| A61K 9/28 | (2006.01) | |

(52) U.S. Cl.
CPC .......... *A61K 9/2095* (2013.01); *A61K 9/2059* (2013.01); *A61K 31/437* (2013.01); *A61K 31/439* (2013.01); *A61K 9/2866* (2013.01)

(58) Field of Classification Search
CPC ...... A61K 31/437; A61K 31/439; A61K 9/20; A61K 9/50
See application file for complete search history.

(56) References Cited

U.S. PATENT DOCUMENTS

| | | | |
|---|---|---|---|
| 4,341,785 A | 7/1982 | Marchi et al. | 424/256 |
| 7,045,620 B2 | 5/2006 | Viscomi et al. | 540/456 |
| 7,902,206 B2 | 3/2011 | Viscomi et al. | 514/279 |
| 7,915,275 B2 | 3/2011 | Viscomi et al. | 514/279 |
| 8,193,196 B2 | 6/2012 | Viscomi et al. | 514/254.11 |
| 9,186,355 B2 * | 11/2015 | Hotha | C07D 498/22 |
| 2005/0272754 A1 * | 12/2005 | Viscomi | C07D 498/22 514/279 |
| 2008/0132530 A1 * | 6/2008 | Viscomi et al. | 514/279 |
| 2011/0105550 A1 | 5/2011 | Gushurst et al. | 514/279 |
| 2012/0059023 A1 | 3/2012 | Viscomi et al. | 514/279 |

FOREIGN PATENT DOCUMENTS

| | | | |
|---|---|---|---|
| WO | WO 2008/029208 | 3/2008 | A61K 9/16 |
| WO | WO 2011/107970 | 9/2011 | A61K 9/20 |
| WO | WO 2012/038898 | 3/2012 | A61K 9/16 |

OTHER PUBLICATIONS

Helmy et al., "Characterization and Quantitation of Aprepitant Drug Substance Polymorphs by Attenuated Total Reflectance Fourier Transform Infrared Spectroscopy," *Analytical Chemistry*, 75(3):605-611 (2003).

Byrn et al., "Pharmaceutical Solids: A Strategic Approach to Regulatory Considerations," *Pharmaceutical Research*, 12(7):945-954 (1995).

Viscomi et al., "Crystal forms of rifaximin and their effect on pharmaceutical properties," *CrystEngComm*, 10:1074-1081 (2008).

* cited by examiner

Primary Examiner — Shirley V Gembeh

(57) ABSTRACT

The present invention relates to stable pharmaceutical compositions comprising rifaximin and processes for their preparation.

6 Claims, No Drawings

PHARMACEUTICAL COMPOSITIONS OF RIFAXIMIN

FIELD OF THE INVENTION

The present invention relates to stable pharmaceutical compositions comprising rifaximin and processes for their preparation.

BACKGROUND OF THE INVENTION

Rifaximin is disclosed in U.S. Pat. No. 4,341,785, and is a non-aminoglycoside semi-synthetic, non-systemic antibacterial related to rifamycin. Chemically, rifaximin is designated as (2S,16Z,18E,20S,21S,22R,23R,24R,25S,26S,27S,28E)-5,6,21,23,25-pentahydroxy-27-methoxy-2,4,11,16,20,22,24,26-octamethyl-2,7-(epoxypentadeca-[1,11,13]trienimino)benzofuro[4,5-e]pyrido[1,2-$\alpha$]-benzimidazole-1,15(2H)-dione,25-acetate. Rifaximin is commercially available in the United States as tablets for oral administration under the trade name of Xifaxan® in dosage strengths of 200 mg and 550 mg. The dosage strength of 200 mg is indicated for the treatment of patients ($\geq$12 years of age) with traveler's diarrhea caused by invasive strains of *Escherichia coli* and the dosage strength of 550 mg is indicated for the reduction in risk of overt hepatic encephalopathy (HE) recurrence in patients $\geq$18 years of age.

As a drug can exist in various polymorphic forms with a significant difference in their pharmacological and toxicological properties along with variable bioavailabilities, it remains a challenge for a formulator to maintain the polymorphic integrity of the drug during the entire shelf-life of the drug, so that the end user consistently gets the same desired effect upon repeated administration. Also, it is required from the drug regulatory agencies to have the manufacturing methods of the drugs standardized and controlled in such a way that these give homogeneous results in terms of polymorphism. The importance of maintaining the same polymorphic form becomes high in cases where there is a rapid conversion of one polymorphic form to another governed by numerous factors and where there exists a significant difference amongst the pharmacological and toxicological properties of the drug.

U.S. Pat. No. 7,045,620 discloses purified polymorphic forms of rifaximin designated as Form $\alpha$, Form $\beta$, and Form $\gamma$. It also discloses that the formation of these polymorphic forms could depend upon numerous factors, such as the presence of water within a crystallization solvent, the temperature at which the product is crystallized, and the amount of water present in the product at the end of the drying process. It further discloses that the presence of water in rifaximin in the solid state is reversible, such that the water absorption and/or release can take place under specific ambient conditions leading to a change in the polymorphic forms. Therefore, rifaximin is susceptible to transition from one form to another form even in the solid state, irrespective of the process involving the steps of dissolution and crystallization. This also stresses the fact that during the phase of preservation of the final rifaximin product, special care needs to be taken so that the ambient conditions do not change the water content of the product.

U.S. Pat. No. 8,193,196 discloses polymorphic forms of rifaximin designated as Form $\delta$ and Form $\epsilon$. It further discloses that these two polymorphic forms show significant differences in terms of bioavailability leading to different pharmacological and toxicological behaviors. It also discloses the tendency of transformation of rifaximin polymorphic form $\delta$ to polymorphic form $\epsilon$ by a drying process.

U.S. Pat. No. 7,902,206 discloses rifaximin in polymorphic forms designated as Form $\alpha$, Form $\beta$, or Form $\gamma$, wherein each form is free of any other polymorphic forms.

U.S. Pat. No. 7,915,275 discloses pharmaceutical compositions comprising an effective amount of a rifaximin polymorph and a pharmaceutically acceptable carrier. It further discloses that the compositions may contain any of the polymorphic forms such as Form $\alpha$, Form $\beta$, or Form $\gamma$, or a mixture of more than one of these polymorphic forms. The mixture may be selected, for example, on the basis of desired amounts of systemic absorption, dissolution profile, and desired location in the digestive tract to be treated.

U.S. Application No. 2012/0059023 claims a method of preparing a pharmaceutical composition having a controlled systemic absorption of rifaximin, by combining two or more polymorphic forms of rifaximin such as Form $\alpha$, Form $\beta$, and Form $\gamma$. It further discloses that the level of systemic rifaximin absorption can be modulated by administering distinct polymorphic forms of rifaximin.

A review of the art thus shows that rifaximin exists in various polymorphic forms with significant different pharmacological and toxicological behaviors, and with variable bioavailabilties. These polymorphic forms are susceptible to transformation from one form to another, even in a solid state at ambient conditions. The modification in the amounts of these different polymorphic forms in the finished pharmaceutical composition is highly critical as any variation in their amount during the shelf-life of the composition will directly affect the bioavailability of rifaximin in patients. Therefore, it is essential to prevent any modification of the polymorphic forms of rifaximin during the shelf-life of the finished pharmaceutical composition. The present inventors have now developed a pharmaceutical composition of rifaximin comprising a specific mixture of polymorphic forms of rifaximin which shows good stability in the relative polymorphic distribution ratio of these polymorphs, and which provides uniform therapeutic effect when administered to the patients.

SUMMARY OF THE INVENTION

The present invention provides stable pharmaceutical compositions of rifaximin comprising a specific mixture of polymorphic forms of rifaximin, i.e., a mixture of Form $\alpha$ and Form $\beta$ of rifaximin in a particular relative polymorphic distribution ratio. It is expected that the particular relative polymorphic distribution ratio of these polymorphic forms would remain stable throughout the shelf-life of the compositions, and thus would provide end users with a uniform therapeutic effect. It further provides processes for the preparation of these stable pharmaceutical compositions.

DETAILED DESCRIPTION OF THE INVENTION

A first aspect of the present invention provides a stable pharmaceutical composition of rifaximin comprising:

(i) a mixture of Form $\alpha$ and Form $\beta$ of rifaximin; and (ii) one or more pharmaceutically acceptable excipients, wherein the relative polymorphic distribution ratio of Form $\alpha$ to Form $\beta$ is from about 15:85 to about 85:15, and wherein said ratio remains substantially unchanged in the pharmaceutical composition after exposure to a relative humidity of 75% and a temperature of 40° C. for at least three months.

According to one embodiment of the above aspect, there is provided a stable pharmaceutical composition of rifaximin comprising:
(i) a mixture of Form α and Form β of rifaximin; and
(ii) one or more pharmaceutically acceptable excipients, wherein the relative polymorphic distribution ratio of Form α to Form β is from about 30:70 to about 70:30, and wherein said ratio remains substantially unchanged in the pharmaceutical composition after exposure to a relative humidity of 75% and a temperature of 40° C. for at least three months.

According to another embodiment of the above aspect, there is provided a stable pharmaceutical composition of rifaximin comprising:
(i) a mixture of Form α and Form β of rifaximin; and
(ii) one or more pharmaceutically acceptable excipients, wherein the relative polymorphic distribution ratio of Form α to Form β is from about 40:60 to about 60:40, and wherein said ratio remains substantially unchanged in the pharmaceutical composition after exposure to a relative humidity of 75% and a temperature of 40° C. for at least three months.

According to another embodiment of the above aspect, there is provided a stable pharmaceutical composition of rifaximin comprising:
(i) a mixture of Form α and Form β of rifaximin; and
(ii) one or more pharmaceutically acceptable excipients, wherein the relative polymorphic distribution ratio of Form α to Form β is about 40:60, and wherein said ratio remains substantially unchanged in the pharmaceutical composition after exposure to a relative humidity of 75% and a temperature of 40° C. for at least three months.

According to another embodiment of the above aspect, there is provided a stable pharmaceutical composition of rifaximin, wherein the pharmaceutically acceptable excipients are selected from the group comprising diluents, disintegrants, binders, lubricants, glidants, or mixtures thereof.

A second aspect of the present invention provides a process for the preparation of a stable pharmaceutical composition of rifaximin, wherein the process comprises the steps of:
(i) blending rifaximin with one or more of pharmaceutically acceptable excipients; and
(ii) compressing the blend of step (i) into a tablet using appropriate tooling.

A third aspect of the present invention provides a process for the preparation of a stable pharmaceutical composition of rifaximin, wherein the process comprises the steps of:
(i) blending rifaximin with one or more of pharmaceutically acceptable excipients;
(ii) dry granulating the blend of step (i) to obtain granules; and
(iii) compressing the granules of step (ii) into a tablet using appropriate tooling.

According to one embodiment of the above aspect, there is provided a process for the preparation of a stable pharmaceutical composition of rifaximin, wherein the process comprises the steps of:
(i) blending rifaximin with one or more of pharmaceutically acceptable excipients;
(ii) compacting the blend of step (i) in a suitable compactor to form the compacts;
(iii) milling the compacts of step (ii) using a suitable mill to obtain granules;
(iv) blending the granules of step (iii) with one or more pharmaceutically acceptable excipients; and
(v) compressing the blend of step (iv) into a tablet using appropriate tooling.

The term "stable", as used herein, refers to a physical stability which means that the relative polymorphic distribution ratio of Form α to Form β in the pharmaceutical composition would remain substantially unchanged as determined by X-ray powder diffraction after exposure to a relative humidity of 75% and a temperature of 40° C., for a period of at least three months.

The term "substantially", as used herein, means the change in the relative polymorphic distribution ratio of Form α to Form β in the pharmaceutical composition is within ±10% of the initial value, preferably within ±5% of the initial value.

The terms "Form α" and "Form β" of rifaximin, as used herein, refer to the two known polymorphic forms of rifaximin, identified and characterized in U.S. Pat. No. 7,045,620, the disclosure of which is incorporated herein by reference in its entirety.

The term "relative polymorphic distribution ratio", as used herein, refers to the amount of Form α and Form β relative to each other in the pharmaceutical composition. The relative polymorphic distribution ratio of the present invention is expected to remain substantially unchanged subsequent to the manufacturing process through the entire shelf-life of the pharmaceutical composition.

The term "about", as used herein, refers to any value which lies within the range defined by a variation of up to ±10% of the value.

The term "pharmaceutical composition", as used herein, includes tablets, capsules, pills, or granules. Preferably, the pharmaceutical composition of the present invention is a tablet.

The term "pharmaceutically acceptable excipients", as used herein, includes excipients that may be added intragranularly and/or extragranularly in the pharmaceutical compositions. The pharmaceutically acceptable excipients are selected from the group comprising diluents, disintegrants, binders, lubricants, glidants, or mixtures thereof.

Suitable diluents are selected from the group comprising lactose, microcrystalline cellulose, starch, pregelatinized starch, calcium sulphate, calcium carbonate, powdered cellulose, mannitol, sorbitol, xylitol, lactitol, dicalcium phosphate, tricalcium phosphate, or mixtures thereof.

Suitable disintegrants are selected from the group comprising croscarmellose sodium, sodium starch glycolate, microcrystalline cellulose, crospovidone, polyvinyl pyrrolidone, low-substituted hydroxypropyl cellulose, alginic acid, calcium salts and potassium salts of carboxymethyl cellulose, colloidal silicon dioxide, guar gum, magnesium aluminum silicate, methylcellulose, powdered cellulose, starch, sodium alginate, or mixtures thereof.

Suitable binders are selected from the group comprising microcrystalline cellulose, polyvinylpyrrolidone, polyethylene glycols, polyvinyl acetate, polyvinyl alcohol, propylene glycol, starch and its derivatives such as corn starch, carboxymethyl cellulose, methylcellulose, hydroxypropyl cellulose, hydroxypropylmethyl cellulose, or mixtures thereof.

Suitable lubricants are selected from the group comprising magnesium stearate, calcium stearate, zinc stearate, sodium stearyl fumarate, powdered stearic acid, magnesium oleate, calcium palmitate, potassium laureate, talc, glycerol monostearate, glycerol distearate, glycerol tristearate, glycerol tripalmitate, glycerol trimyristate, glycerol tribehenate, glycerol palmitate stearate, glycerol behenate, or mixtures thereof.

Suitable glidants are selected from the group comprising colloidal silica, magnesium trisilicate, powdered cellulose, talc, tribasic calcium phosphate, or mixtures thereof.

The manufacturing process of the pharmaceutical composition is critical as it could lead to a change in the relative polymorphic distribution ratio during the shelf-life of the pharmaceutical composition. The stable pharmaceutical compositions of the present invention are prepared by dry methods, such as direct compression and dry granulation. The dry granulation method may involve the use of a Chilsonator®, a suitable compactor, or the formation of slugs.

The pharmaceutical composition of the present invention may be further coated with one or more functional or non-functional coating layers. Preferably, the pharmaceutical composition is coated with one or more non-functional coating layers. The coating layers may comprise one or more film-forming polymers and coating additives.

Examples of film-forming polymers include cellulose and its derivatives such as ethyl cellulose, hydroxypropylmethyl cellulose, e.g., hypromellose 5 cP and hypromellose 15 cP, hydroxypropyl cellulose, methyl cellulose, carboxymethyl cellulose, hydroxymethyl cellulose, hydroxyethyl cellulose, cellulose acetate, hydroxypropyl methyl cellulose phthalate, cellulose acetate phthalate, cellulose acetate trimellitate; waxes; and methacrylic acid polymers, e.g., Eudragit®, and the like. Alternatively, commercially available coating compositions comprising film-forming polymers marketed under various trade names, such as Opadry®, may also be used.

Coating additives may be selected from the group consisting of binders, plasticizers, chelating agents, coloring agents, lubricants, opacifiers, or mixtures thereof.

Suitable plasticizers are selected from the group consisting of triethyl citrate, dibutyl sebacate, acetylated triacetin, tributyl citrate, glycerol tributyrate, monoglyceride, rapeseed oil, olive oil, sesame oil, acetyl tributyl citrate, acetyl triethyl citrate, glycerin sorbitol, diethyl oxalate, diethyl phthalate, diethyl malate, diethyl fumarate, dibutyl succinate, diethyl malonate, dioctyl phthalate, or mixtures thereof.

Suitable chelating agents are selected from the group consisting of ethylenediamine tetraacetic acid, or derivatives or salts thereof, e.g., disodium edetate; dihydroxyethyl glycine; glucamine; acids, e.g., citric acid, tartaric acid, gluconic acid, and phosphoric acid; or mixtures thereof.

Coloring agents includes any FDA approved color for oral use such as iron oxide, titanium dioxide, zinc oxide, or mixtures thereof.

Suitable opacifiers are selected from the group consisting of titanium dioxide, manganese dioxide, iron oxide, silicon dioxide, or mixtures thereof.

Specific examples of solvents for coating include purified water, acetone, ethanol, isopropyl alcohol, methylene chloride, or combinations thereof.

Coating may be performed by applying the coating composition as a solution/suspension/blend using any conventional coating technique known in the art, such as spray coating in a conventional coating pan or fluidized bed processor, dip coating, or compression coating.

The invention may be further illustrated by the following examples, which are for illustrative purposes only and should not be construed as limiting the scope of the invention in any way.

EXAMPLES

Example 1

| Ingredients | Quantity (mg/tablet) |
|---|---|
| Rifaximin | 550.00 |
| Microcrystalline cellulose | 313.75 |
| Sodium starch glycolate | 41.25 |
| Colloidal silicon dioxide | 2.75 |
| Glyceryl distearate | 49.50 |
| Talc | 2.75 |
| Magnesium stearate | 5.00 |
| Film Coating | |
| Opadry ® | 25.00 |
| Purified water | q.s. |
| Total Weight | 990.00 mg |

Procedure:
1. Rifaximin was sifted through a suitable sieve and blended with microcrystalline cellulose, sodium starch glycolate, and colloidal silicon dioxide in a suitable blender.
2. The blend of step 1 was blended with glyceryl diasterate.
3. The blend of step 2 was compacted in a suitable compactor to form a compact.
4. The compact of step 3 was comminuted using a suitable mill to obtain granules.
5. The granules of step 4 were sifted through a suitable sieve to obtain granules and fines which were repeatedly compacted, comminuted, and sieved until the desired granules to fines ratio was obtained.
6. The granules of step 5 were blended with microcrystalline cellulose, sodium starch glycolate, and colloidal silicon dioxide.
7. The blend of step 6 was lubricated with talc, glyceryl distearate, and magnesium stearate.
8. The lubricated blend of step 7 was compressed into a tablet.
9. Opadry® was dispersed in purified water.
10. The tablet of step 8 was coated in a conventional coating pan using the coating dispersion of step 9.

Example 2

| Ingredients | Quantity (mg/tablet) |
|---|---|
| Rifaximin | 550.00 |
| Microcrystalline cellulose | 316.25 |
| Sodium starch glycolate | 41.25 |
| Colloidal silicon dioxide | 2.75 |
| Glyceryl distearate | 49.50 |
| Talc | 2.75 |
| Magnesium stearate | 5.00 |
| Film Coating | |
| Hypromellose 5 cP | 10.51 |
| Hypromellose 15 cP | 9.92 |
| Titanium dioxide | 5.95 |

-continued

| | Quantity (mg/tablet) |
|---|---|
| Propylene glycol | 1.98 |
| Iron oxide red | 0.60 |
| Disodium edetate | 0.08 |
| Purified water | q.s. |
| Total Weight | 996.54 mg |

Procedure:
1. Rifaximin was sifted through a suitable sieve, and blended with microcrystalline cellulose, sodium starch glycolate, and colloidal silicon dioxide in a suitable blender.
2. The blend of step 1 was blended with glyceryl diasterate.
3. The blend of step 2 was compacted in a suitable compactor to form a compact.
4. The compact of step 3 was comminuted using a suitable mill to obtain granules.
5. The granules of step 4 were sifted through a suitable sieve to obtain granules and fines which were repeatedly compacted, comminuted, and sieved until the desired granules to fines ratio was obtained.
6. The granules of step 5 were blended with microcrystalline cellulose, sodium starch glycolate, and colloidal silicon dioxide.
7. The blend of step 6 was lubricated with talc, glyceryl distearate, and magnesium stearate.
8. The lubricated blend of step 7 was compressed into a tablet.
9. Disodium edetate and propylene glycol were dissolved in purified water.
10. Hypromellose 5 cP, hypromellose 15 cP, titanium dioxide, and iron oxide red were dispersed into the solution of step 9.
11. The tablet of step 8 was coated in a conventional coating pan using the coating dispersion of step 10.

Example 3

| Ingredients | Quantity (mg/tablet) |
|---|---|
| Rifaximin | 550.00 |
| Microcrystalline cellulose | 313.75 |
| Sodium starch glycolate | 41.25 |
| Colloidal silicon dioxide | 2.75 |
| Glyceryl distearate | 49.50 |
| Talc | 2.75 |
| Magnesium stearate | 5.00 |
| Film Coating | |
| Opadry ® | 28.95 |
| Purified water | q.s. |
| Total Weight | 993.95 mg |

Procedure:
1. Rifaximin was sifted through a suitable sieve and blended with microcrystalline cellulose, sodium starch glycolate, and colloidal silicon dioxide in a suitable blender.
2. The blend of step 1 was blended with glyceryl diasterate.
3. The blend of step 2 was compacted in a suitable compactor to form a compact.
4. The compact of step 3 was comminuted using a suitable mill to obtain granules.
5. The granules of step 4 were sifted through a suitable sieve to obtain granules and fines which were repeatedly compacted, comminuted, and sieved until the desired granules to fines ratio was obtained.
6. The granules of step 5 were blended with microcrystalline cellulose, sodium starch glycolate, and colloidal silicon dioxide.
7. The blend of step 6 was lubricated with talc, glyceryl distearate, and magnesium stearate.
8. The lubricated blend of step 7 was compressed into a tablet.
9. Opadry® was dispersed in purified water.
10. The tablet of step 8 was coated in a conventional coating pan using the coating dispersion of step 9.

Stability Data

The tablets prepared according to Example 1, Example 2, and Example 3 were stored at a relative humidity of 75% and a temperature of 40° C. for a period of three months, and analyzed for relative polymorphic distribution ratio of Form α and Form β determined through X-ray powder diffraction method. The results of the analysis are represented in Table 1.

TABLE 1

Results of the Stability Study of the Tablets Prepared According to Examples 1, 2, and 3 Stored at Relative Humidity of 75% and a Temperature of 40° C.

| Condition | Example 1 | | Example 2 | | Example 3 | |
|---|---|---|---|---|---|---|
| | Form α | Form β | Form α | Form β | Form α | Form β |
| Initial | 38.47 | 61.53 | 74.37 | 25.63 | 59.65 | 40.35 |
| One month | 39.09 | 60.91 | 71.53 | 28.47 | — | — |
| Three months | 37.98 | 62.02 | 73.76 | 26.24 | 57.11 | 42.89 |

From the above table, it is clear that the relative polymorphic distribution ratio of Form α and Form β remained substantially unchanged for a period of three months, which shows that the pharmaceutical compositions prepared according to Example 1, Example 2, and Example 3 remained stable for three months.

We claim:
1. A stable pharmaceutical composition of rifaximin comprising:
   (i) a mixture of Form α and Form β of rifaximin; and
   (ii) one or more pharmaceutically acceptable excipients, wherein the relative polymorphic distribution ratio of Form α to Form β is from 15:85 to 85:15, and wherein said ratio remains substantially unchanged in the pharmaceutical composition after exposure to a relative humidity of 75% and a temperature of 40° C. for at least three months.
2. The stable pharmaceutical composition according to claim 1, wherein the relative polymorphic distribution ratio of Form α to Form β is from 30:70 to 70:30.
3. The stable pharmaceutical composition according to claim 2, wherein the relative polymorphic distribution ratio of Form α to Form β is from 40:60 to 60:40.
4. The stable pharmaceutical composition according to claim 3, wherein the relative polymorphic distribution ratio of Form α to Form β is about 40:60.
5. The stable pharmaceutical composition according to claim 1, wherein the pharmaceutically acceptable excipients are selected from the group comprising diluents, disintegrants, binders, lubricants, glidants, or mixtures thereof.

6. The stable pharmaceutical composition according to claim 1, wherein the pharmaceutical composition is selected from the group comprising tablets, capsules, pills, or granules.

* * * * *